United States Patent
Gustafsson

(10) Patent No.: US 10,129,667 B2
(45) Date of Patent: Nov. 13, 2018

(54) MULTI-POLE MAGNETIC COUPLING FOR BONE CONDUCTION DEVICE

(71) Applicant: COCHLEAR LIMITED, Macquarie University (AU)

(72) Inventor: Johan Gustafsson, Mölnlycke (SE)

(73) Assignee: COCHLEAR LIMITED, Macquarie University (AU)

( * ) Notice: Subject to any disclaimer, the term of this patent is extended or adjusted under 35 U.S.C. 154(b) by 0 days.

(21) Appl. No.: 15/440,593

(22) Filed: Feb. 23, 2017

(65) Prior Publication Data

US 2017/0251313 A1 Aug. 31, 2017

Related U.S. Application Data

(60) Provisional application No. 62/300,605, filed on Feb. 26, 2016.

(51) Int. Cl.
*H04R 25/00* (2006.01)
*A61N 1/08* (2006.01)
*A61N 1/375* (2006.01)

(52) U.S. Cl.
CPC .............. *H04R 25/606* (2013.01); *A61N 1/08* (2013.01); *A61N 1/375* (2013.01); *H04R 2225/67* (2013.01); *H04R 2460/13* (2013.01)

(58) Field of Classification Search
CPC .............. H04R 25/606; H04R 2225/67; H04R 2460/13

USPC ............................................. 600/25; 381/326
See application file for complete search history.

(56) References Cited

U.S. PATENT DOCUMENTS

| | | | |
|---|---|---|---|
| 2004/0210103 A1 | 10/2004 | Westerkull | |
| 2007/0053536 A1* | 3/2007 | Westerkull | H04R 25/606 381/326 |
| 2011/0264172 A1* | 10/2011 | Zimmerling | A61N 1/3718 607/60 |
| 2012/0029267 A1* | 2/2012 | Ball | H04R 25/606 600/25 |
| 2012/0229235 A1 | 9/2012 | Fullerton et al. | |
| 2012/0229241 A1 | 9/2012 | Fullerton et al. | |
| 2012/0246885 A1 | 10/2012 | Fullerton et al. | |
| 2014/0012069 A1* | 1/2014 | Ball | A61N 1/375 600/25 |
| 2014/0012071 A1* | 1/2014 | Nagl | A61N 1/375 600/25 |
| 2014/0121450 A1* | 5/2014 | Kasic | H04R 25/60 600/25 |

* cited by examiner

*Primary Examiner* — Sunita Joshi
(74) *Attorney, Agent, or Firm* — Merchant & Gould P.C.

(57) ABSTRACT

A percutaneous bone conduction auditory prosthesis utilizes a multipole magnetic coupling system to secure the external device to an abutment that is secured to the skull of a recipient. With the multipole magnetic coupling system, a very strong retention force is formed between the device and the abutment. The multipole magnetic coupling system can include a complex array of exposed poles, such that the retention forces are coordinated with a mating abutment.

20 Claims, 8 Drawing Sheets

MULTI-POLE MAGNETIC COUPLING FOR BONE CONDUCTION DEVICE

CROSS-REFERENCE TO RELATED APPLICATION

This application claims the benefit of U.S. Provisional Patent Application No. 62/300,605, filed Feb. 26, 2016, entitled "MULTI-POLE MAGNETIC COUPLING FOR BONE CONDUCTION DEVICE". The disclosure of this priority application is hereby incorporated by reference in its entirety herein for any and all purposes.

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea function normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

In percutaneous bone conduction auditory prostheses, a multipole magnetic coupling system can be utilized to secure the external device to an abutment that is secured to the skull of a recipient. By using a multipole magnet, a very strong retention force is formed. Additionally, the multipole magnet can have a complex array of exposed poles, such that the retention forces are optimized with a mating abutment. As such, this can help ensure that only abutments from a desired manufacturer are used with devices from that manufacturer, and vice versa.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

DETAILED DESCRIPTION

Figure 1A:
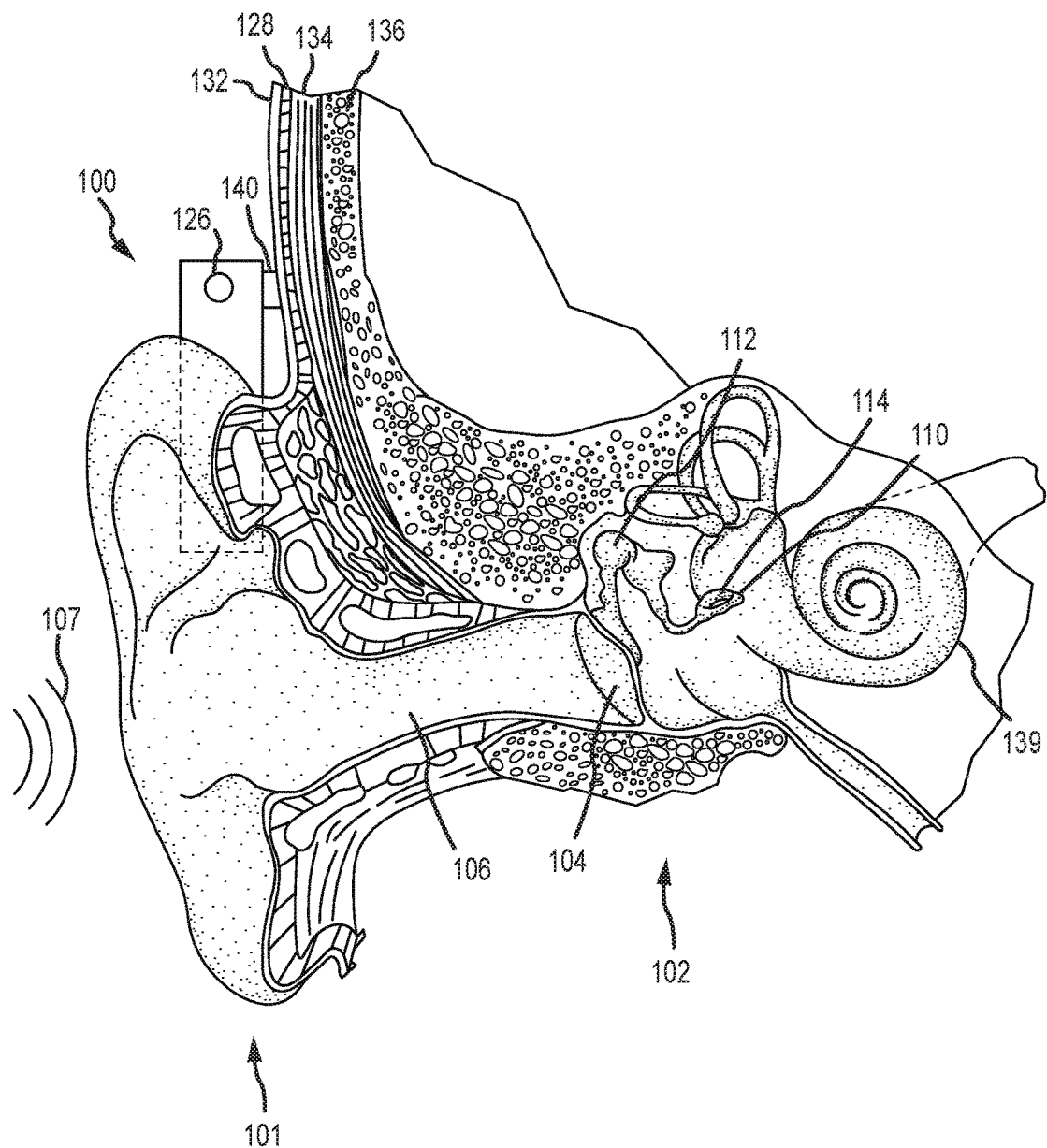
FIG. 1A depicts a partial perspective view of a percutaneous bone conduction device worn on a recipient.

The magnetic coupling technologies described herein can typically be utilized with bone conduction devices, more specifically, percutaneous bone conduction devices that anchor directly to a recipient's skull. Such coupling technologies incorporate magnets formed into a single coupling element, or a permanent magnet formed with multiple discrete poles. Such magnetic coupling systems generate an attraction force that has a certain "reach," which helps the recipient properly position the bone conduction device on their abutment. Put another way, the magnetic coupling system helps "pull" the device towards the correct location and orientation. Additionally, magnetic coupling systems can be generally more wear-resistant, as compared to conventional snap couplings typically used for percutaneous bone conduction devices. Snap couplings utilize mechanical parts that degrade with repetitive use and may need to be replaced, which in turn can adversely affect sound transmission characteristics and efficiency. Such wear can also cause feedback problems. Coupling systems using multiple magnetic poles further concentrate magnetic flux at the surface of the magnet, and a stronger magnetic force is created, thus improving sound transmission and device retention.

The use of a multipole magnetic coupling system for a percutaneous bone conduction device generates a higher attraction force per volume of magnetic material. As such, the size of the coupling can be reduced, if desired. Additionally, the poles of the multipole coupling system can be magnetized in a specific pattern of magnetic poles so that matching poles on the opposite side of the system are needed to generate a sufficient retention force.

The multipole magnetic coupling systems described herein can comprise a plurality of discrete magnets joined together. They can also comprise a plurality of magnets formed in a unitary block of material. In the first example, discrete magnets (e.g., in a rod configuration with north and south polarities on opposite ends) are bound or joined together so as to form a single body having multiple exposed poles. The individual magnets can be positioned to create a common surface that contains a plurality of the exposed poles. This is typically an outer surface of the component body. In the second example, a single magnetic component is magnetized using a specific magnetization pulse so as to form multiple individual magnetic elements (magnetic poles) on the surface. Such magnetic elements can be referred to a "magnetic domains." Each magnetic element can be configured so as to have a north pole, a south pole, or can have no polarity (e.g., display a neutral charge).

The individual magnets or magnetic elements can vary in terms of which pole is exposed on a particular surface of the component. Thus, a single component can have multiple distinct magnetic poles on a single surface, and these multiple magnetic poles can be arranged to form a pattern of north and south poles. Moreover, a single unitary component having multiple magnetic domains can be programmed or reprogrammed by applying an electromagnetic pulse to one or more magnetic poles to form (or change) the magnetized surface pattern. Depending on the size, polarity, and the strength of the electromagnetic pulse, the size and polarity of the magnetic domains can be changed. Thus, the pattern of magnetization can be changed.

FIG. 1A depicts a partial perspective view of a percutaneous bone conduction device 100 positioned behind outer ear 101 of the recipient and comprises an input element 126 to receive sound signals 107. The input element 126 can be a microphone for receiving actual sounds, or can be a telecoil or input port for receiving electrical signals corresponding to sounds that have been received at an associated device that includes a sound processor. In the present example, input element 126 can be located, for example, on or in bone conduction device 100. Also, bone conduction device 100 includes a digital sound processor (not shown) that processes the sounds received by the input element 126, a vibrating electromagnetic actuator and/or various other operational components, as described below.

More particularly, the illustrated input device 126 includes a microphone that converts received sound signals into electrical signals. These electrical signals are processed by the sound processor. The sound processor generates control signals that cause the actuator to vibrate. In other words, the actuator converts the electrical signals into mechanical force to impart vibrations to skull bone 136 of the recipient.

Bone conduction device 100 further includes a transmission element 140, e.g., in the form of an actuator shaft, that transfers vibrations from the bone conduction device to the recipient. The illustrated transmission element 140 includes a magnetic coupling system to attach bone conduction device 100 to the recipient. In the example of FIG. 1A, the magnetic coupling system of transmission element 140 is attached to an anchor system (not shown) implanted in the recipient. An exemplary anchor system (also referred to as a fixation system) can include a percutaneous abutment fixed to the recipient's skull bone 136. The abutment extends from skull bone 136 through muscle 134, fat 128 and skin 132 so that transmission element 140 can be attached thereto. The percutaneous abutment includes a mating magnetic coupling system, examples of which are described below. These paired magnetic coupling systems facilitate efficient transmission of mechanical force.

As described above, the input element 126 can include devices other than a microphone, such as, for example, an input port, cable termination (for an integrated cable system) or other form of connection, etc. In an example, input element 126 is an electrical port that connects to a remote sound processor, such as a so-called behind-the-ear (BTE) device that hangs from the recipient's ear or body worn component. In such a case, the remote sound processor can include a microphone and electronics module for processing received sounds. Signals corresponding thereto can be sent to the bone conduction device 100 via a cable that is part of or connected to the input element 126, which can be in the form of a female port to receive a compatible male connector. Input element 126 can receive a sound signal in the form of an electrical signal from an MP3 player or a smartphone electronically connected to sound input element 126 via a wired or wireless connection.

In cases where the input element 126 is a microphone and the bone conduction device 100 includes an on-board sound processing unit, the sound processing unit processes the output of the input element 126, which is typically in the form of an electrical signal. The processing unit generates control signals that cause an associated actuator to vibrate. In other words, the actuator converts the electrical signals into mechanical vibrations for delivery to the recipient's skull. These mechanical vibrations are delivered by an external portion of the auditory prosthesis 100, as described below.

Figure 1B:
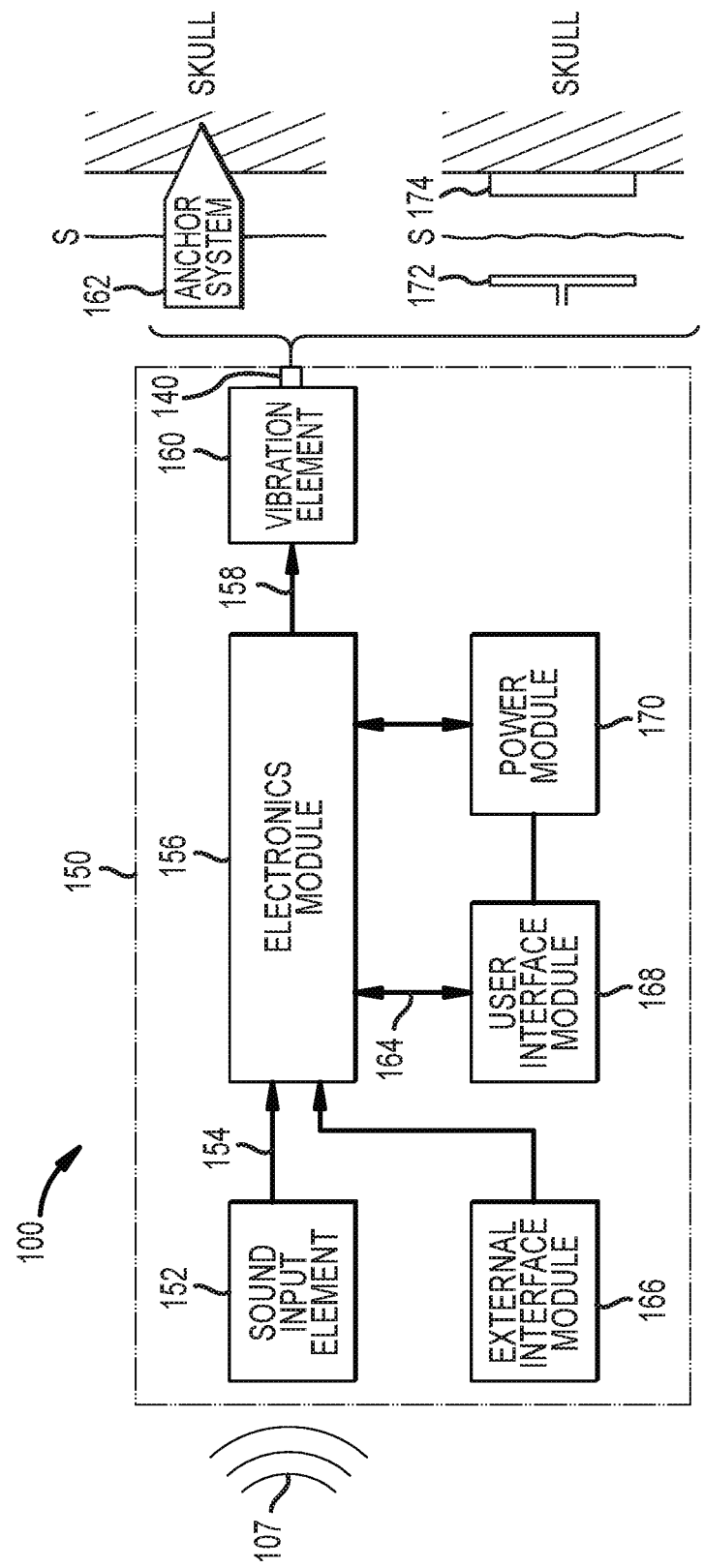
FIG. 1B is a schematic diagram of a bone conduction device.

FIG. 1B is a schematic diagram of a bone conduction device 100 that may be either a percutaneous or transcutaneous bone conduction device. Sound 107 is received by sound input element 152. In the depicted example, sound input element 152 is a microphone configured to receive sound 107, and to convert sound 107 into electrical signal 154. Alternatively, sound 107 is received by sound input element 152 as an electrical signal. As shown in FIG. 1B, electrical signal 154 is output by sound input element 152 to electronics module 156. Electronics module 156 is configured to convert electrical signal 154 into adjusted electrical signal 158. As described below in more detail, electronics module 156 can include a sound processor, control electronics, transducer drive components, and a variety of other elements.

As shown in FIG. 1B, vibration element or actuator 160 receives adjusted electrical signal 158 and generates a mechanical output force in the form of vibrations that are delivered to the skull of the recipient via a transmission element 140, often in the form of a shaft extending from the vibration actuator 160. Transmission of vibration can be via a number of different systems, depending on the type of bone conduction device. For example, in a percutaneous bone conduction device, the transmission element 140 can be connected to an anchor system 162, such as a bone screw that penetrates the skin S of the recipient and is secured directly to the skull. In a transcutaneous bone conduction device, the transmission element 140 can be connected to a transmission plate 172 that is disposed against the skin S of the recipient. This plate 172 is magnetically engaged with an implanted magnet 174, so as to transmit vibrations to the skull. Engagement between the transmission element 140 and either the bone screw 162 or the transmission plate 172 is often via a mechanical engagement device (e.g., a snap connector). The multi-pole magnetic coupling systems described herein are utilized in lieu of, or to supplement, a mechanical engagement device that joins the transmission element 140 with either the bone screw 160 or the transmission plate 172. Delivery of an output force causes motion or vibration of the recipient's skull, thereby activating the hair cells in the recipient's cochlea (not shown) via cochlea fluid motion.

FIG. 1B also illustrates power module 170. Power module 170 provides electrical power to one or more components of bone conduction device 100. For ease of illustration, power module 170 has been shown connected only to user interface module 168 and electronics module 156. However, it should be appreciated that power module 170 can be used to supply power to any electrically powered circuits/components of bone conduction device 100.

User interface module 168, which is included in bone conduction device 100, allows the recipient to interact with bone conduction device 100. For example, user interface module 168 can allow the recipient to adjust the volume, alter the speech processing strategies, power on/off the device, etc. In the example of FIG. 1B, user interface module 168 communicates with electronics module 156 via signal line 164.

Bone conduction device 100 can further include external interface module that can be used to connect electronics module 156 to an external device, such as a fitting system. Using external interface module 166, the external device, can obtain information from the bone conduction device 100 (e.g., the current parameters, data, alarms, etc.) and/or modify the parameters of the bone conduction device 100 used in processing received sounds and/or performing other functions.

In the example of FIG. 1B, sound input element 152, electronics module 156, vibration element 160, power module 170, user interface module 168, and external interface module have been shown as integrated in a single housing, referred to as housing 150. However, it should be appreciated that in certain examples, one or more of the illustrated components can be housed in separate or different housings. For example, the sound input element 152 and electronics module 156 can be disposed in a BTE device that is physically isolated from the actuator. Similarly, it should also be appreciated that in such aspects, direct connections between the various modules and devices are not necessary and that the components can communicate, for example, via wireless connections.

FIGS. 2-7 depict examples of multipole magnetic coupling systems that can be utilized in conjunction with a percutaneous bone conduction device. Only percutaneous bone conduction devices are depicted for clarity. As described above, multipole magnetic coupling systems can also be used with transcutaneous bone conduction devices, e.g., to join the transmission element 140 to the transmission plate 172. Additionally, the multipole magnetic coupling systems described herein have applications in other technologies. These are but examples to explain some of the functionality and benefits of multipole magnetic coupling systems. As such, other configurations, orientations and arrangements of poles, etc., are contemplated. In view of the teachings herein, additional functionality and benefits will also be apparent to a person of skill in the art.

Figure 2:
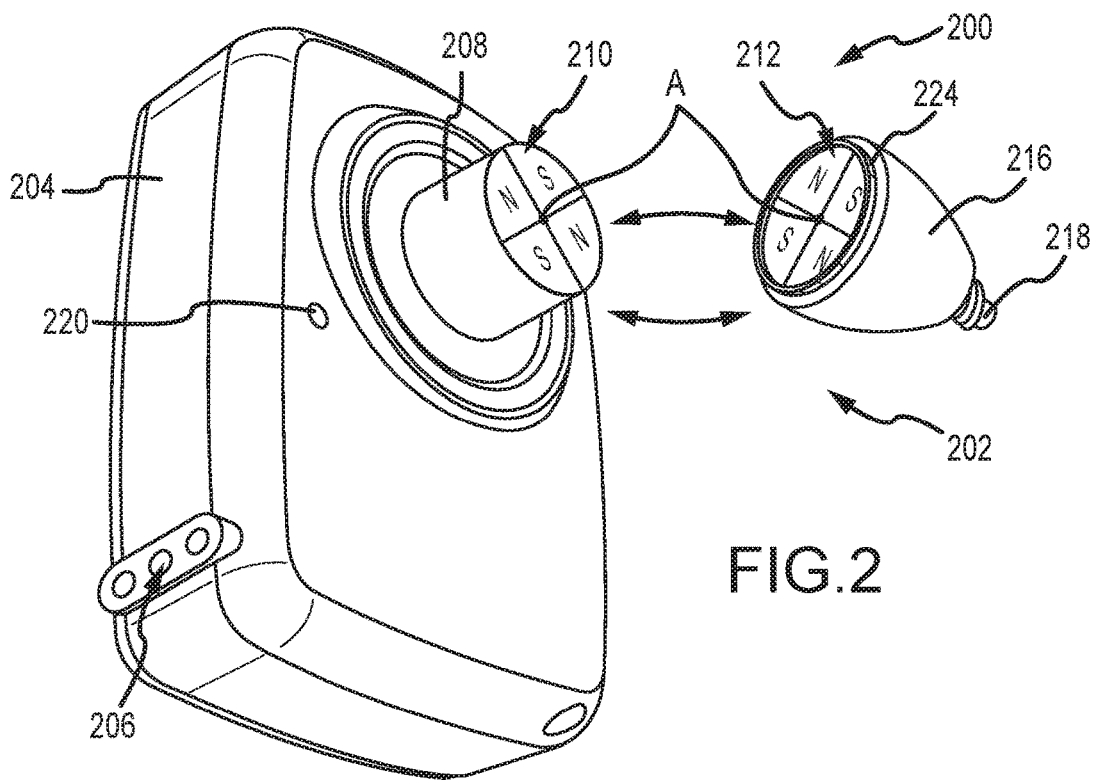
FIGS. 2-7 depict examples of multipole magnetic coupling systems that can be utilized in conjunction with percutaneous bone conduction devices.

FIG. 2 depicts an example of a multipole magnetic coupling system 200 that can be utilized in conjunction with a percutaneous bone conduction device 202. The device 202 includes a bone conduction device housing 204. The housing 204 can include the various components as described above with regard to FIGS. 1A and 1B. The housing 204 defines at least one input element 206. The input element 206 can be a port or opening defined by the housing 204 that is in communication with an internal sound input element such as a microphone. In another example, the input element 206 can be a female connector that allows a remote device (e.g., a BTE device, MP3 player, smartphone, etc.) to be connected to the bone conduction device housing 204, e.g., via a cable. In another example, the input element 206 can be a co-axial connector part or a cable integrated with the housing 204. In the examples described herein, however, an input element 206 in the form of a port in communication with a microphone is generally described for clarity. In examples, multiple microphones (e.g., two) having multiple input ports 206 are utilized in a bone conduction device 202. The orientation of the two input ports relative to each other defines the direction from which sounds are reinforced when the device 202 is set in a directionality mode. Only a single input port 206 is described herein for illustrative purposes.

An actuator shaft 208 extends from the housing 204 and is connected to a vibration actuator within the housing 204 as described above. The actuator shaft 208 includes a shaft magnetic engagement surface 210 disposed on an end of the actuator shaft 208 that is opposite the vibration actuator or housing 204. For actuator shafts having straight outer side surfaces, however, the shaft magnetic engagement surface 210 can be disposed on one or more of such side surfaces. In other examples, the shaft magnetic engagement surface 210 and the abutment magnetic engagement surface 212 need not be flat surfaces, as depicted. Mating convex and concave surfaces are contemplated, as are mating conical surfaces. In another example, one of the engagement surfaces can include a key projecting therefrom while the opposite surface can define a keyhole to help expedite alignment. In another example, a raised collar 224 can extend from, e.g., the abutment 216 so as to surround the shaft 208 to help ensure alignment. However, the multipole magnetic coupling systems described herein can enable alignment between the shaft magnetic engagement surface 210 and an abutment magnetic engagement surface 212 disposed on an abutment 216. This alignment obviates the need for any collar or other mechanical structure that would otherwise be used to ensure alignment. As such, the raised collar 224 need not be used and is not depicted in the remaining examples. The abutment 216 can include a threaded securement element 218 on an end of the abutment 216 opposite the abutment magnetic engagement surface 212. The threaded securement element 218 is utilized to engage the abutment 216 to the skull. Together, the shaft magnetic engagement surface 210 and the abutment magnetic engagement surface 212 form the multipole magnetic coupling system 200.

Each of the shaft magnetic engagement surface 210 and the abutment magnetic engagement surface 212 include a plurality of exposed poles, depicted generally as north poles N and south poles S. Neutral, non-charged, poles (or non-magnetic material) can also be utilized but are not depicted here. As described above, each magnetic surface 210, 212 can be manufactured of multiple discrete magnets joined together or can be a magnet having multiple exposed poles. The poles on the shaft magnetic engagement surface 210 are arranged in a pattern that is a mirror image of a pattern on the abutment magnetic engagement surface 212. However, within the mirror image, the polarities at discrete locations of the pattern on the shaft magnetic engagement surface 210 are opposite the polarities at mirrored locations on the abutment magnetic engagement surface 212. As such, the north poles N on one engagement surface 212, 210 mate magnetically with the south poles on the other engagement surface 212, 210. The actuator shaft 208 and the abutment 216 each include an axis A that substantially align when the shaft magnetic engagement surface 210 and the abutment magnetic engagement surface 212 are engaged. The arrangement of the poles on each of the shaft magnetic engagement surface 210 and the abutment magnetic engagement surface 212 can be characterized in various ways. For example, in FIG. 2, the poles are arranged in a pie- or grid-like pattern, having alternating north N and south S poles. In another characterization, the poles are arranged symmetrically about each axis A. In that regard, the poles are arranged in an alternating (e.g., north-south-north-south layout) circumferentially about the axis A. The symmetrical layout can also be described as systematic or as a fixed, predictable pattern, or a regular or repeating pattern.

The symmetrical layout displays other advantages. For example, the symmetrical arrangement allows the shaft magnetic engagement surface 210 to engage with the abutment magnetic engagement surface 212 in a plurality of discrete positions relative to and about the axis A. Since two north poles N are located as depicted on the shaft magnetic engagement surface 210, these two north poles N can mate with either of the alternating two south poles S on the abutment magnetic engagement surface 212. As such, this magnet configuration allows the actuator shaft 208 to be oriented in a plurality of positions about the axis A. Thus, the attachment force is equal at multiple angular configurations between the shaft magnetic engagement surface 210 and the abutment magnetic engagement surface 212. Thus, a recipient can change the position of engagement if required or desired. For example, in one orientation, it is possible that the device housing 204 can interfere with a hat worn by the recipient. In such a case, the recipient can reposition the shaft magnetic engagement surface 210 relative to the abutment magnetic engagement surface 212 so as to eliminate or reduce the interference.

The bone conduction device 202 can also include a sensor 220, which can be a magnetic field sensor. The magnetic field sensor 220 can detect a presence and/or a characteristic of a magnetic field formed by the multipole magnetic coupling system 200. If a system 200 having particular predetermined characteristics is detected, the sensor 220 can send a signal to the sound processor disposed within the housing. This signal can communicate information to the sound processor or other internal component for a number of purposes. For example, the information can be analyzed so as to determine a magnetic pattern of, e.g., the abutment magnetic engagement surface 212 or the multiple magnetic coupling system 200 as a whole. For example, the recipient can have a left-side abutment with a first magnetic pattern, and a right-side abutment with a second, different magnetic pattern. Upon attachment to the abutment, the device 202 can identify the magnetic pattern to determine the side of the head upon which it is disposed. Device settings based thereon can be adjusted accordingly, since bone conduction devices 202 can be configured to operate differently on different sides of the head. Thus, a bilateral recipient (a recipient who wears bone conduction devices on both sides of the head) need not remember which device needs to be placed on which side of the head in order to maintain desired functionality. The magnetic field sensor 220 can also be utilized to detect an exact arrangement or pattern of poles on the abutment magnetic engagement surface 212. If the detected pole arrangement is recognized, the device 202 can initiate operation, for example, or take another action. In another example, the sensor 220 can detect the presence of an RFID tag disposed, for example, in the abutment 216. Detection of a predetermined RFID tag can result in an adjustment of device settings, or other actions.

Figure 3:
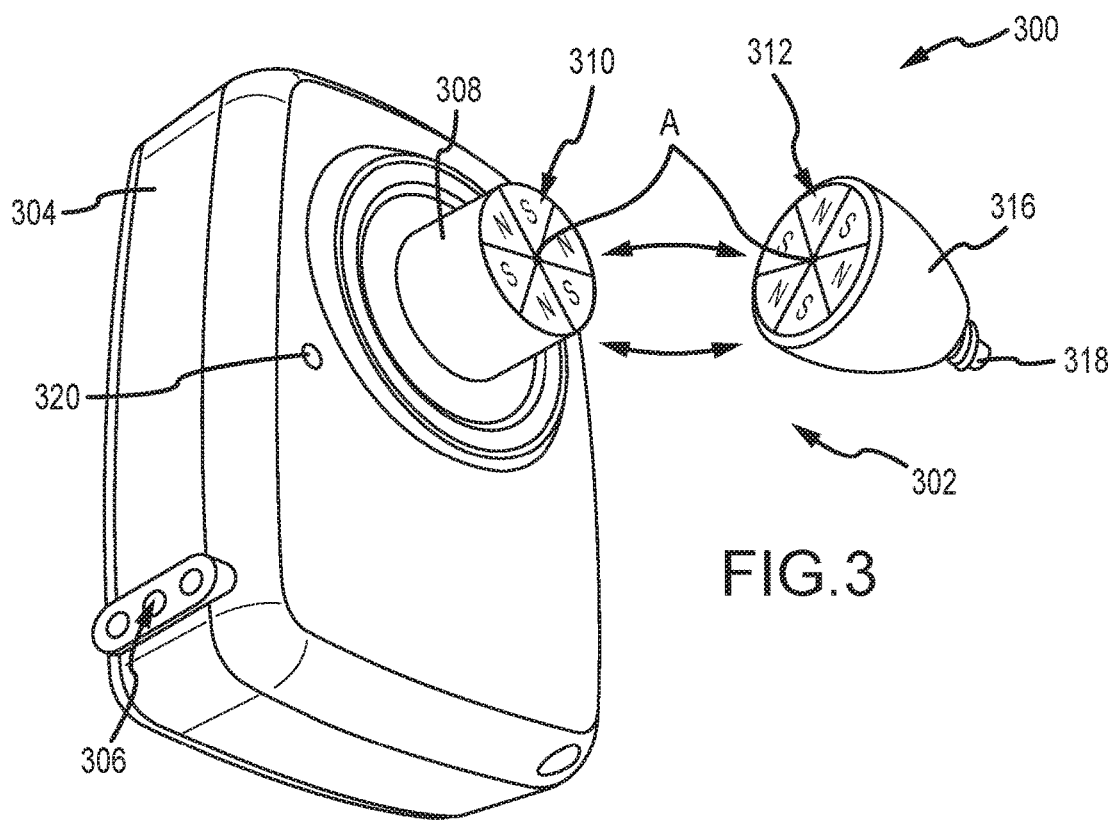

FIG. 3 depicts another example of a multipole magnetic coupling system 300 that can be utilized in conjunction with a percutaneous bone conduction device 302. Many of the components in FIG. 3 are described above with regard to FIG. 2 and, as such, are not necessarily described further. Additional disclosure regarding certain specific components is provided. The device 302 includes a bone conduction device housing 304 that can include the various components as described above with regard to FIGS. 1A and 1B. The housing 304 defines at least one input port 306 that is in communication with a microphone or a connector (e.g., a female connector) that allows connection of a remote device via a cable. Only a single input port 306 is described herein, even though multiple ports can be utilized. An actuator shaft 308 extends from the housing 304 and is connected to a vibration actuator within the housing 304. The actuator shaft 308 includes a shaft magnetic engagement surface 310 and can be configured in a variety of contours and shapes. The shaft magnetic engagement surface 310 is configured to magnetically engage with an abutment magnetic engagement surface 312 disposed on an abutment 316. The abutment 316 can include a threaded securement element 318 that is utilized to engage the abutment 316 to the skull. Together, the shaft magnetic engagement surface 310 and the abutment magnetic engagement surface 312 form the multipole magnetic coupling system 300. The bone conduction device 302 can also include a sensor 320, which can be a magnetic field sensor or RFID sensor.

Each of the shaft magnetic engagement surface 310 and the abutment magnetic engagement surface 312 can include a plurality of exposed poles: north N, south S, or neutral (not depicted). The poles on the shaft magnetic engagement surface 310 are arranged in a pattern that is a mirror image of a pattern of poles on the abutment magnetic engagement surface 312, but with opposite polarities at corresponding locations on the mirror image pattern. The actuator shaft 308 and the abutment 316 each include an axis A that substantially align. In the depicted configuration, the poles are arranged in a pie-like pattern, having alternating north N and south S poles. Additionally, the poles are arranged symmetrically about each axis A. This allows the shaft magnetic engagement surface 310 to engage with the abutment magnetic engagement surface 312 in a plurality of discrete positions relative to and about the axis A. Since three north poles N are configured as depicted on the shaft magnetic engagement surface 310, three discrete positions or orientations between the device housing 304 and the abutment 316 are possible. As such, this magnet configuration allows the actuator shaft 308 to be oriented in a plurality of positions about the axis A.

Figure 4:
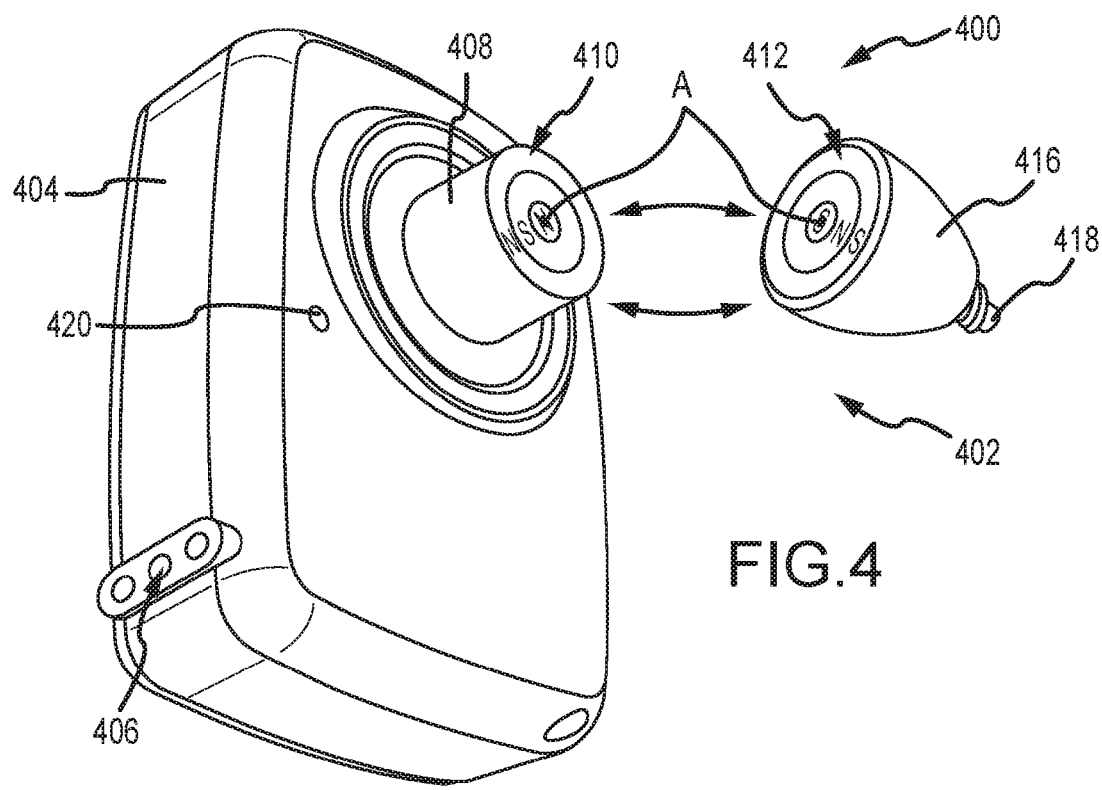

FIG. 4 depicts another example of a multipole magnetic coupling system 400 that can be utilized in conjunction with a percutaneous bone conduction device 402. Many of the components in FIG. 4 are described above with regard to FIG. 2 and, as such, are not necessarily described further. Additional disclosure regarding certain specific components is provided. The device 402 includes a bone conduction device housing 404 that can include the various components as described above with regard to FIGS. 1A and 1B. The housing 404 defines at least one input port 406 that is in communication with a microphone or a connector that allows connection of a remote device via a cable. Only a single input port 406 is described herein, even though multiple ports can be utilized. An actuator shaft 408 extends from the housing 404 and is connected to a vibration actuator within the housing 404. The actuator shaft 408 includes a shaft magnetic engagement surface 410 and can be configured in a variety of contours and shapes. The shaft magnetic engagement surface 410 is configured to matingly magnetically engage with an abutment magnetic engagement surface 412 disposed on an abutment 416. The abutment 416 can include a threaded securement element 418 that is utilized to engage the abutment 416 to the skull. Together, the shaft magnetic engagement surface 410 and the abutment magnetic engagement surface 412 form the multipole magnetic coupling system 400. The bone conduction device 402 can also include a sensor 420, which can be a magnetic field sensor or RFID sensor.

Each of the shaft magnetic engagement surface 410 and the abutment magnetic engagement surface 412 can include a plurality of exposed poles: north N, south S, or neutral (not depicted). The poles on the shaft magnetic engagement surface 410 are arranged in a pattern that is a mirror image of a pattern of poles on the abutment magnetic engagement surface 412, but with opposite polarities at corresponding locations on the mirror image pattern. The actuator shaft 408 and the abutment 416 each include an axis A that substantially align. In the depicted configuration, the poles are arranged in a pattern of concentric circles, having alternating north N and south S poles radiating outward from the axis A. As such, the poles are arranged symmetrically about each axis A. This allows the shaft magnetic engagement surface 410 to engage with the abutment magnetic engagement surface 412 in a substantially infinite number of discrete positions relative to and about the axis A. This magnet configuration displays rotational symmetry about the axis A, such that the attachment force is equal regardless of the angular configuration.

Figure 5:
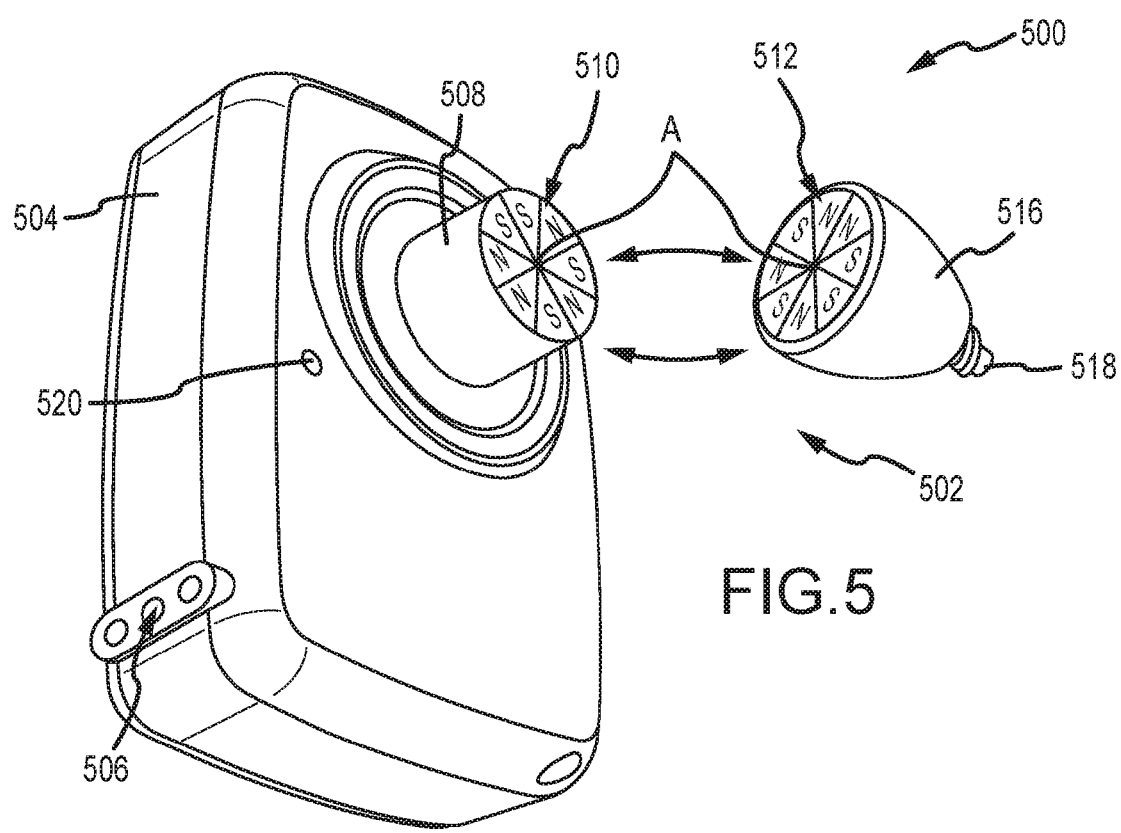

FIG. 5 depicts another example of a multipole magnetic coupling system 500 that can be utilized in conjunction with a percutaneous bone conduction device 502. Many of the components in FIG. 5 are described above with regard to FIG. 2 and, as such, are not necessarily described further. Additional disclosure regarding certain specific components is provided. The device 502 includes a bone conduction device housing 504 that can include the various components as described above with regard to FIGS. 1A and 1B. The housing 504 defines at least one input port 506 that is in communication with a microphone or a connector that allows connection of a remote device via a cable. Only a single input port 506 is described herein, even though multiple ports can be utilized. An actuator shaft 508 extends from the housing 504 and is connected to a vibration actuator within the housing 504. The actuator shaft 508 includes a shaft magnetic engagement surface 510 and can be configured in a variety of contours and shapes. The shaft magnetic engagement surface 510 is configured to matingly magnetically engage with an abutment magnetic engagement surface 512 disposed on an abutment 516. The abutment 516 can include a threaded securement element 518 that is utilized to engage the abutment 516 to the skull. Together, the shaft magnetic engagement surface 510 and the abutment magnetic engagement surface 512 form the multipole magnetic coupling system 500. The bone conduction device 502 can also include a sensor 520, which can be a magnetic field sensor or RFID sensor.

Each of the shaft magnetic engagement surface 510 and the abutment magnetic engagement surface 512 can include a plurality of exposed poles: north N, south S, or neutral (not depicted). The poles on the shaft magnetic engagement surface 510 are arranged in a pattern that is a mirror image of a pattern of poles on the abutment magnetic engagement surface 512, but with opposite polarities at corresponding locations on the mirror image. The actuator shaft 508 and the abutment 516 each include an axis A that substantially align. In the depicted configuration, the poles are arranged in a pie-like pattern. Unlike the previous examples, however, the north N and south S poles are arranged irregularly about the axis A. This asymmetrical arrangement about each axis A allows the shaft magnetic engagement surface 510 to engage with the abutment magnetic engagement surface 512 in only a single position relative to and about the axis A. Indeed, the force of the opposing magnets will impart repulsion forces on the actuator shaft 508, thus effectively forcing the device housing 504 into the single mating position. Advantages of such a magnet configuration are described elsewhere herein.

Figure 6:
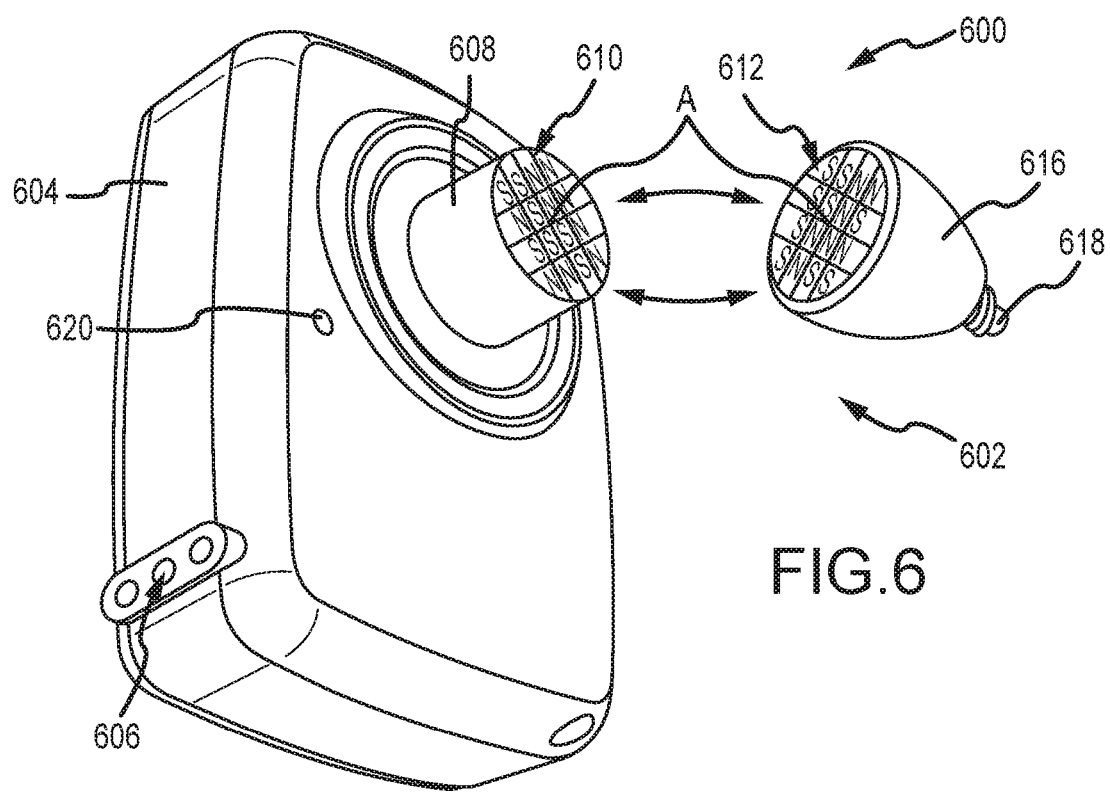

FIG. 6 depicts another example of a multipole magnetic coupling system 600 that can be utilized in conjunction with a percutaneous bone conduction device 602. Many of the components in FIG. 6 are described above with regard to FIG. 2 and, as such, are not necessarily described further. Additional disclosure regarding certain specific components is provided. The device 602 includes a bone conduction device housing 604 that can include the various components as described above with regard to FIGS. 1A and 1B. The housing 604 defines at least one input port 606 that is in communication with a microphone or a connector that allows connection of a remote device via a cable. Only a single input port 606 is described herein, even though multiple ports can be utilized. An actuator shaft 608 extends from the housing 604 and is connected to a vibration actuator within the housing 604. The actuator shaft 608 includes a shaft magnetic engagement surface 610 and can be configured in a variety of contours or shapes. The shaft magnetic engagement surface 610 is configured to matingly magnetically engage with an abutment magnetic engagement surface 612 disposed on an abutment 616. The abutment 616 can include a threaded securement element 618 that is utilized to engage the abutment 616 to the skull. Together, the shaft magnetic engagement surface 610 and the abutment magnetic engagement surface 612 form the multipole magnetic coupling system 600. The bone conduction device 602 can also include a sensor 620, which can be a magnetic field sensor or RFID sensor.

Each of the shaft magnetic engagement surface 610 and the abutment magnetic engagement surface 612 can include a plurality of exposed poles: north N, south S, or neutral (not depicted). The poles on the shaft magnetic engagement surface 610 are arranged in a pattern that is a mirror image of a pattern of poles on the abutment magnetic engagement surface 612, but with opposite polarities at corresponding locations on the mirror image. The actuator shaft 608 and the abutment 616 each include an axis A that substantially align. In the depicted configuration, the poles are arranged in a grid-like pattern. Like the example of FIG. 5, the north N and south S poles are arranged randomly about the axis A. This asymmetrical arrangement about each axis A allows the shaft magnetic engagement surface 610 to engage with the abutment magnetic engagement surface 612 in only a single position relative to and about the axis A. Advantages of such a magnet configuration are described elsewhere herein. The four-by-four grid array depicted in FIG. 6 is particularly advantageous, since a significant number of magnetic pattern combinations are available. Assuming that only three discrete states or polarities are available: negative (south), positive (north), and neutral, a four-by-four magnetic domain array can have possible magnetization combinations of $3^{16}$=43,046,721. In that regard, many specific magnetized arrays can be made available.

Figure 7:
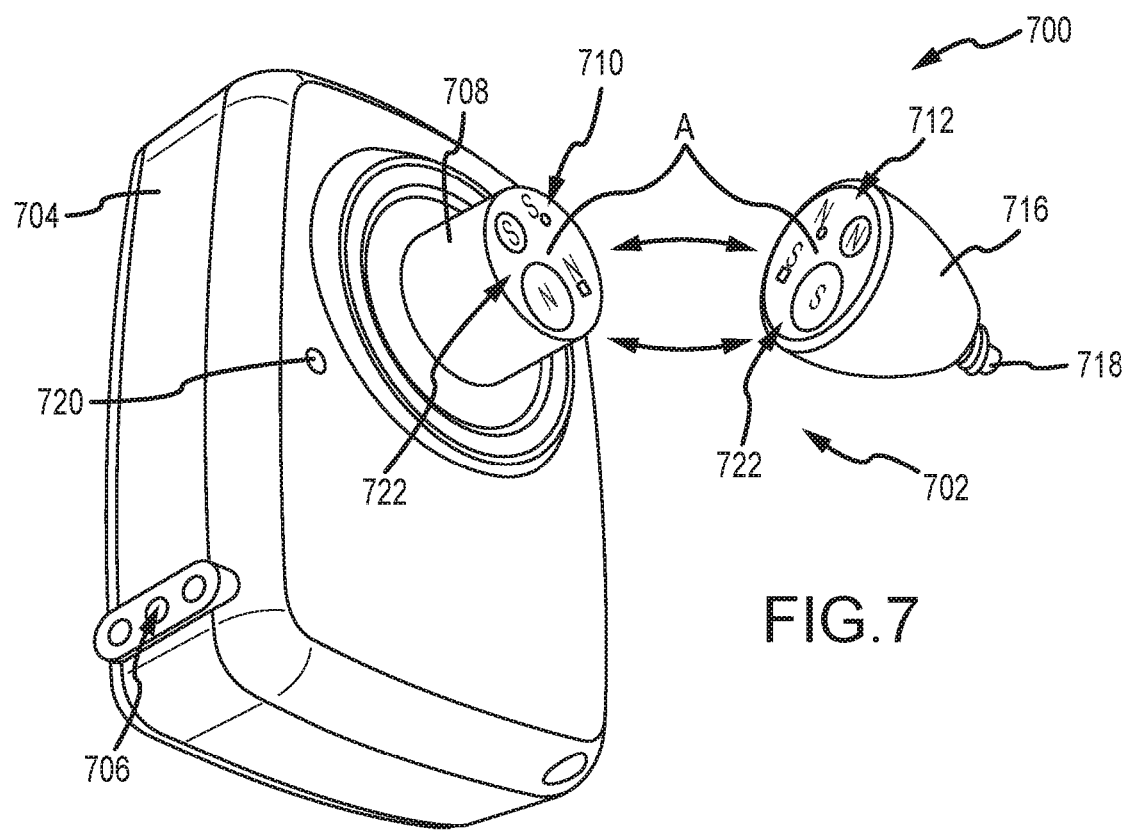

FIG. 7 depicts another example of a multipole magnetic coupling system 700 that can be utilized in conjunction with a percutaneous bone conduction device 702. Many of the components in FIG. 7 are described above with regard to FIG. 2 and, as such, are not necessarily described further. Additional disclosure regarding certain specific components is provided. The device 702 includes a bone conduction device housing 704 that can include the various components as described above with regard to FIGS. 1A and 1B. The housing 704 defines at least one input port 706 that is in communication with a microphone or a connector that allows connection of a remote device via a cable. Only a single input port 706 is described herein, even though multiple ports can be utilized. An actuator shaft 708 extends from the housing 704 and is connected to a vibration actuator within the housing 704. The actuator shaft 708 includes a shaft magnetic engagement surface 710 and can be configured in a variety of contours or shapes. The shaft magnetic engagement surface 710 is configured to matingly magnetically engage with an abutment magnetic engagement surface 712 disposed on an abutment 716. The abutment 716 can include a threaded securement element 718 that is utilized to engage the abutment 716 to the skull. Together, the shaft magnetic engagement surface 710 and the abutment magnetic engagement surface 712 form the multipole magnetic coupling system 700. The bone conduction device 702 can also include a sensor 720, which can be a magnetic field sensor or RFID sensor.

Each of the shaft magnetic engagement surface 710 and the abutment magnetic engagement surface 712 can include a plurality of exposed poles: north N, south S, or neutral (not depicted). The poles on the shaft magnetic engagement surface 710 are arranged in a pattern that is a mirror image of a pattern of poles on the abutment magnetic engagement surface 712, but with opposite polarities at corresponding locations on the mirror image. The actuator shaft 708 and the abutment 716 each include an axis A that substantially align. In the depicted configuration, the poles are arranged in a random pattern about the axis A, where areas of specific polarities are separated by areas of non-magnetic material 722. This can be accomplished, as described above, by adjusting the polarity of magnetic domains continuously between positive and negative. The areas of non-magnetic material 722 can be made neutral. Other discrete portions of the shaft magnetic engagement surface 710 and the abutment magnetic engagement surface 712 can be magnetized to positive and negative. Alternatively, discrete magnets having defined polarities can be surrounded and embedded in a nonmagnetic material, such as a ceramic, stainless steel, or other materials. This asymmetrical arrangement about each axis A allows the shaft magnetic engagement surface 710 to engage with the abutment magnetic engagement surface 712 in only a single position relative to and about the axis A. Given that areas of the surfaces 710, 712 can be magnetized as desired, a virtually infinite number of pattern configurations are possible.

Figure 8:
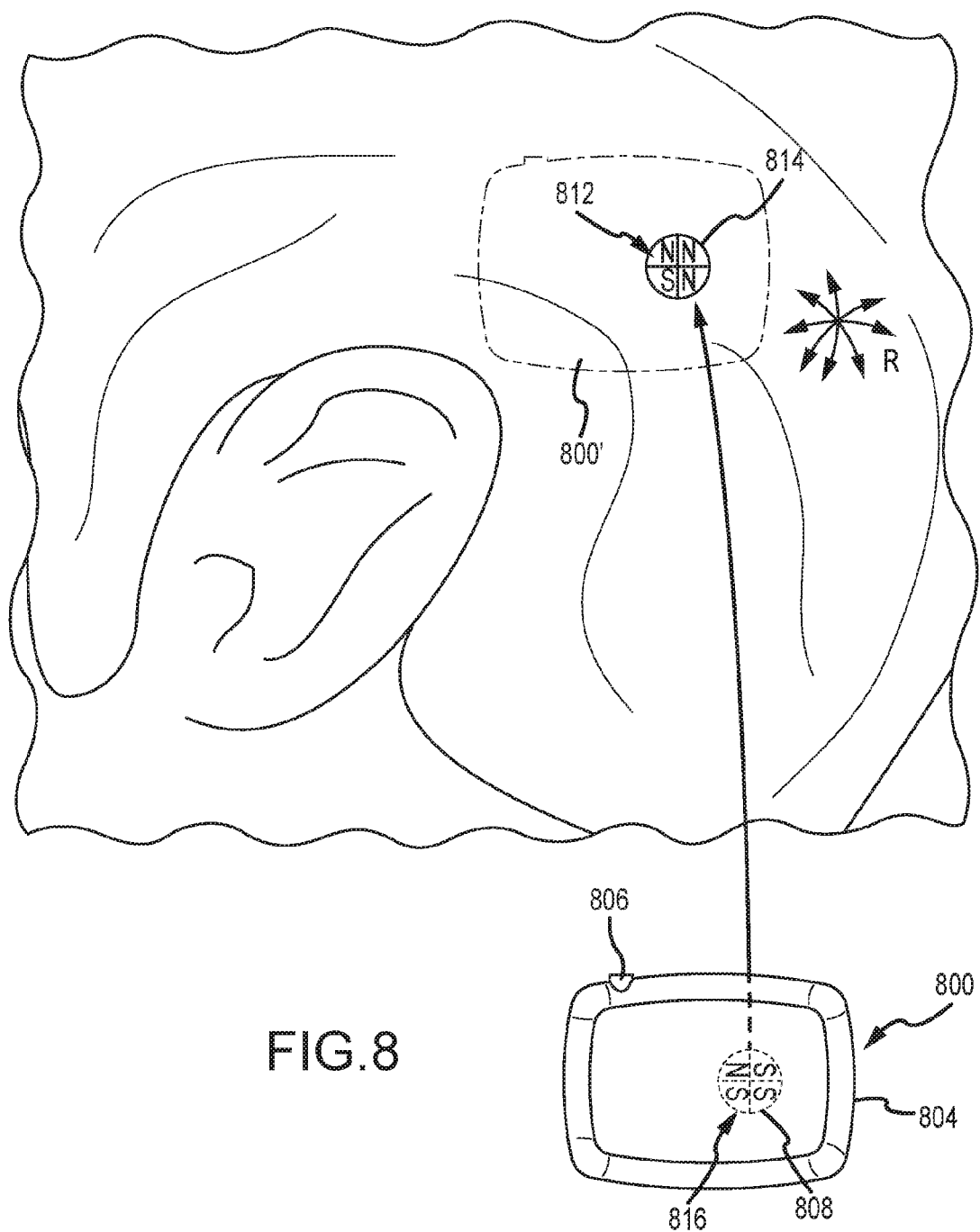
FIGS. 8 and 9 depict a percutaneous bone conduction device utilizing a multipole magnetic coupling system, being placed and worn on a recipient.
Figure 9:
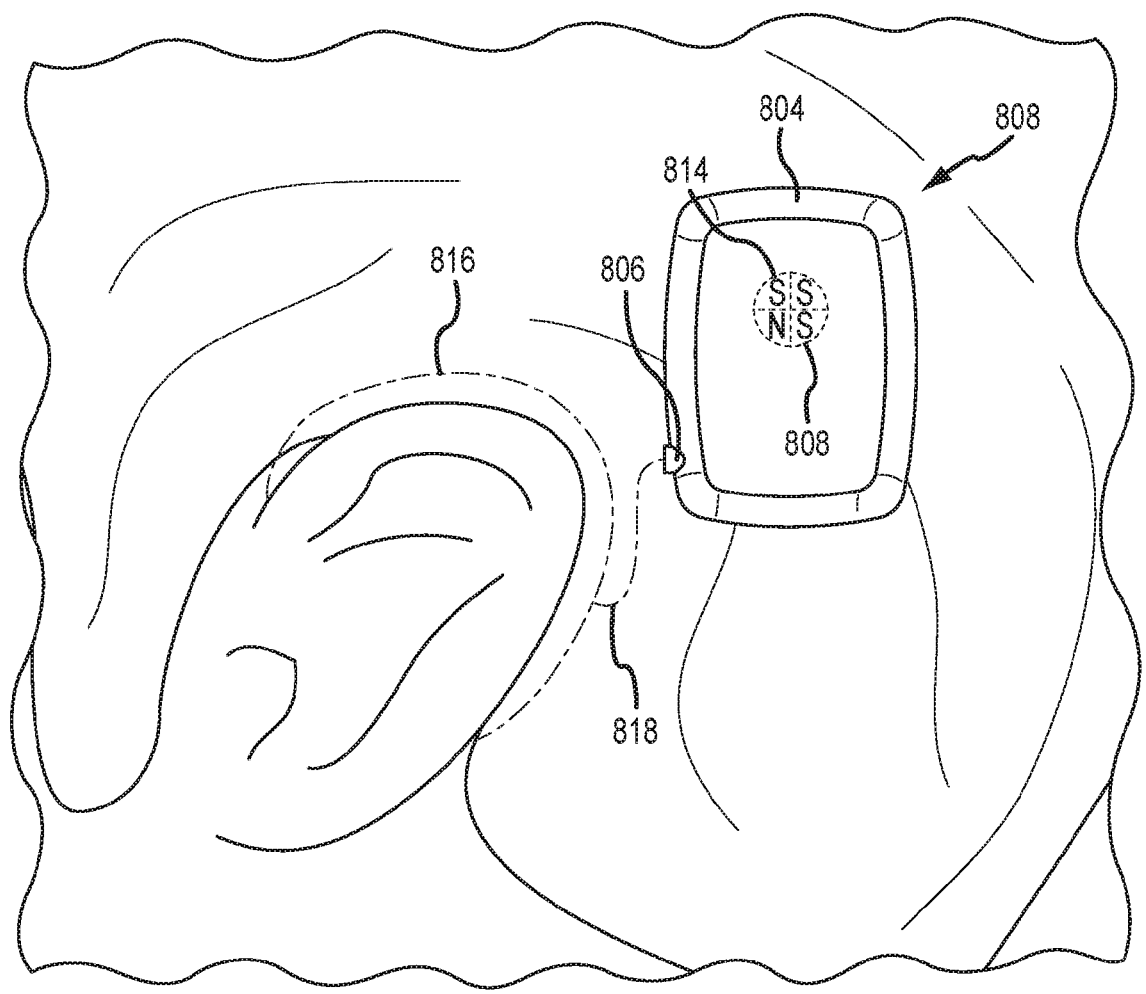

FIGS. 8 and 9 depict a percutaneous bone conduction device 800 utilizing a multipole magnetic coupling system, being placed and worn on a recipient R. The bone conduction device 800 includes a housing 804 that has disposed thereon an input port 806 that can be in communication with a microphone or can be a connector for cable for a remote device. Multiple input ports (e.g., in devices that utilize two or more microphones for sound directionality) may be utilized, but a single input port 806 is depicted here for reference. On an underside of the housing 804 is an actuator shaft 808 that extends therefrom (and is shown in hidden lines). The actuator shaft 808 includes a shaft magnetic engagement surface 810 disposed thereon. The shaft magnetic engagement surface 810 is configured to engage with an abutment magnetic engagement surface 814 disposed on an outer surface of an abutment 814, which is secured to the skull of the recipient R. For illustrative purposes, a grid- or pie-like arrangement of poles is depicted. A single north pole N and three south poles S are depicted on the shaft magnetic engagement surface 810, while opposing poles are depicted on the abutment magnetic engagement surface 814. The magnetized multipole magnetic coupling system can be of any configuration of poles, e.g., as described herein or as would be apparent to a person of skill in the art.

FIG. 8 depicts the recipient placing their bone conduction device 800 on their abutment 814. Since such placement is typically performed without the benefit of a mirror, this step is typically performed by feel. As such, the device 800 is often misaligned when it is first brought proximate the abutment 814. This misalignment is depicted as dashed lines for device 800'. However, given the pattern of poles on the magnetized multipole magnetic coupling system, repulsion forces R will be exerted on the device 800' as the all the poles of shaft magnetic engagement surface 810 simultaneously attempt to align with their opposite poles the abutment magnetic engagement surface 814. This will ultimately compel the proper alignment of the device 800 relative to the skull of the recipient. The repulsion forces between matching poles (e.g., N to N, S to S) and the attraction forces between opposite poles (e.g., N to S, S to N), will ultimately result in the device 800 attaining the single defined alignment available due to the magnetized multipole magnetic coupling system. This is depicted in FIG. 9, where the device 800 is shown attached to the abutment 814.

Since the poles on the abutment magnetic engagement surface 814 are magnetized such that the poles on the shaft magnetic engagement surface 810 can align in only one specific direction, the device 800 can only be oriented on the recipient's head in one specific orientation. As such, since the input port 806 is in a fixed location on the device 800, the input port is only positionable in a single direction, relative to the skull. In the depicted configuration, this orients the input port 806 only facing forward on the head (so as to receive sound, if a microphone is in communication with the input port 806). If the input port is a connector (e.g., to be connected to a BTE 816 with a cable 818) orientation of the device 804 and input port 806 is also advantageous. This helps ensure that the cable 818 does not twist or disconnect, since the device 800 resists rotation.

Multipole magnetic coupling systems, such as those described herein, can display other advantages beyond those described above. For bilateral recipients (recipients that utilize a device on both sides of the head) the multipole magnetic coupling systems can be configured differently for each device/abutment pairing. As such, if the recipient attempts to attach the right-side device to the left-side abutment, the device will be repelled (or at a minimum, will not attach with sufficient robustness), so it cannot be unintentionally attached on the incorrect side. This is relevant because each device can have different settings to achieve different results. In another example, the multipole magnetic coupling systems can also be designed with a complex pole arrangement, which will act like a lock and key. Such complex arrangements and patterns are described above, especially with regard to FIGS. 6 and 7. The magnetized multipole magnetic coupling system can be specific to a particular manufacturer or model, so that the abutment can be utilized only with devices with verified compatible devices so as to guarantee patient expected performance. The multipole magnetic coupling systems can also be individualized so that only a recipient's specific device (with their particular settings) can be attached.

Figure 10:
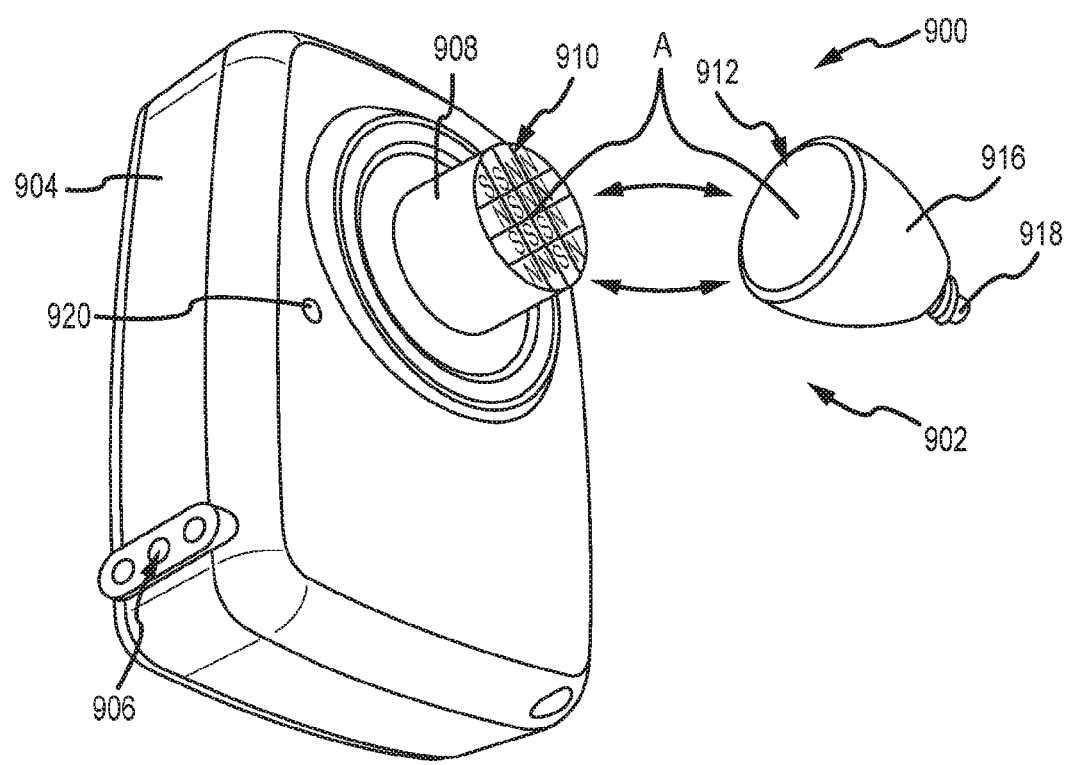
FIG. 10 depicts another example of a multipole magnetic coupling system that can be utilized in conjunction with percutaneous bone conduction devices.

FIG. 10 depicts another example of a multipole magnetic coupling system 900 that can be utilized in conjunction with a percutaneous bone conduction device 902. Many of the components in FIG. 10 are described above with regard to FIG. 2 and, as such, are not necessarily described further. Additional disclosure regarding certain specific components is provided. The device 902 includes a bone conduction device housing 904 that can include the various components as described above with regard to FIGS. 1A and 1B. The housing 904 defines at least one input port 906 that is in communication with a microphone or a connector that allows connection of a remote device via a cable. Only a single input port 906 is described herein, even though multiple ports can be utilized. An actuator shaft 908 extends from the housing 904 and is connected to a vibration actuator within the housing 904. The actuator shaft 908 includes a shaft magnetic engagement surface 910 and can be configured in a variety of contours or shapes. The shaft magnetic engagement surface 910 is configured to matingly magnetically engage with an abutment magnetic engagement surface 912 disposed on an abutment 916. The abutment 916 can include a threaded securement element 918 that is utilized to engage the abutment 916 to the skull. Together, the shaft magnetic engagement surface 910 and the abutment magnetic engagement surface 912 form the multipole magnetic coupling system 900. The bone conduction device 902 can also include a sensor 920, which can be a magnetic field sensor or RFID sensor. In the example of FIG. 10, only the shaft magnetic engagement surface 910 includes a plurality of exposed poles: north N, south S, or neutral (not depicted). The abutment magnetic engagement surface 912 is a soft magnetic material, such as iron. Although precise positioning of the shaft 908 relative to the abutment 916 is not possible with such a configuration, utilizing a shaft multipole magnetic engagement surface 910 with only a soft magnet on the abutment magnetic engagement surface 912 can also be desirable. The multipole shaft magnetic engagement surface 910 (as opposed to a single pole engagement surface) can increase the retention force, even when used in conjunction with the soft magnet. This can enable a reduction in side of the shaft 908 and/or abutment 916, which is also desirable. In other examples, the abutment magnetic engagement surface 912 can utilize a multipole system, while the shaft magnetic coupling surface 910 can be a soft magnet.

This disclosure described some aspects of the present technology with reference to the accompanying drawings, in which only some of the possible aspects were shown. Other aspects, however, can be embodied in many different forms and should not be construed as limited to the examples set forth herein. Rather, these examples were provided so that this disclosure was thorough and complete and fully conveyed the scope of the possible examples to those skilled in the art.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative examples. The scope of the technology is defined by the following claims and any equivalents therein.

What is claimed is:

1. A bone conduction hearing prosthesis comprising a vibration actuator and a magnetic coupling assembly connected to the vibration actuator, wherein the magnetic coupling assembly comprises an engagement surface having a plurality of exposed poles, including both a north pole and a south pole, that is configured to secure the bone conduction hearing prosthesis to a percutaneous abutment and transfer vibrations from the vibration actuator to bone of a recipient to cause a hearing percept.

2. The bone conduction hearing prosthesis of claim 1, wherein the actuator includes an output shaft, the magnetic coupling assembly is disposed on an end of the output shaft, and the magnetic coupling assembly terminates at the engagement surface at a position furthest from the actuator.

3. The bone conduction hearing prosthesis of claim 2, wherein the engagement surface comprises a plurality of north poles and a plurality of south poles disposed symmetrically about a longitudinal axis of the output shaft.

4. The bone conduction hearing prosthesis of claim 1, wherein the engagement surface comprises at least three distinct magnetic poles.

5. The bone conduction hearing prosthesis of claim 1, further comprising:
    the percutaneous abutment, wherein the percutaneous abutment is configured to be secured to bone with a securement element disposed at a first end of the abutment; and
    an abutment magnetic engagement surface disposed at a second end of the abutment opposite the first end,
    wherein the abutment magnetic engagement surface includes a plurality of exposed poles, including both a north pole and a south pole, and wherein the abutment magnetic engagement surface is configured to magnetically engage with the engagement surface of the magnetic coupling assembly.

6. The bone conduction hearing prosthesis of claim 5, wherein the engagement surface of the magnetic coupling assembly is configured to sit flush against the abutment magnetic engagement surface with no overlap between the percutaneous abutment and the magnetic coupling assembly.

7. The bone conduction hearing prosthesis of claim 1, further comprising an actuator shaft defining a shaft axis, wherein the plurality of exposed poles are disposed on the engagement surface so as to enable magnetic engagement between the engagement surface and an abutment magnetic engagement surface at a plurality of discrete positions about the shaft axis.

8. The bone conduction hearing prosthesis of claim 1, wherein the magnetic coupling assembly is configured to support the full weight of the bone conduction hearing prosthesis when the bone conduction hearing prosthesis is worn by a recipient.

9. An apparatus comprising a wearable prosthesis having a housing defining an input port and a magnetic engagement surface configured to secure the wearable prosthesis to a percutaneous abutment,
    wherein the magnetic engagement surface defines a pattern of exposed magnetic poles that are engageable with a reciprocal magnetic engagement surface of the percutaneous abutment such that the input port is positionable only in select positions relative to the percutaneous abutment.

10. The apparatus of claim 9, wherein the percutaneous abutment is configured to be secured to bone with a securement element disposed at a first end of the abutment, the reciprocal magnetic engagement surface of the percutaneous abutment disposed at a second end of the abutment opposite the first end,
    wherein the reciprocal engagement surface includes a plurality of exposed poles arranged reciprocally to the pattern of exposed poles on the magnetic engagement surface of the wearable prosthesis.

11. The apparatus of claim 10, wherein the percutaneous abutment includes a bone screw and the bone screw is configured to be secured to the skull of a recipient.

12. The apparatus of claim 10, wherein the plurality of exposed poles of the reciprocal magnetic engagement surface define a mirror image of the pattern of exposed poles of the magnetic engagement surface of the housing.

13. The apparatus of claim 9, wherein the exposed poles are arranged in one of a grid pattern, a pie pattern or an irregular pattern.

14. The apparatus of claim 9, wherein the wearable prosthesis is configured to be worn on the head of a recipient, and wherein the pattern of the exposed poles restricts positioning of the input port to a single direction relative to the recipient's skull.

15. The apparatus of claim 9, further comprising a magnetic sensor disposed in the housing, wherein the magnetic sensor is configured to detect a magnetic field generated by magnetic engagement of the magnetic engagement surface and the reciprocal magnetic engagement surface.

16. The apparatus of claim 9, wherein the input port comprises at least one of a microphone and a connector port.

17. A wearable prosthesis comprising a housing with electrical components disposed therein and a magnetic assembly configured to secure the housing to a recipient, wherein the magnetic assembly comprises a surface with at least three exposed poles, wherein the exposed poles include both a north pole and a south pole.

18. The wearable prosthesis of claim 17, wherein the at least three exposed poles are arranged in a regular pattern.

19. The wearable prosthesis of claim 17, wherein the at least three exposed poles are separated from each other by a non-magnetic material.

20. The wearable prosthesis of claim 17, wherein the magnetic assembly comprises a plurality of north poles and a plurality of south poles, and the magnetic assembly is configured to support the full weight of the wearable prosthesis when the wearable prosthesis is worn by a recipient.

* * * * *